United States Patent [19]
Lu et al.

[11] Patent Number: 5,784,163
[45] Date of Patent: *Jul. 21, 1998

[54] OPTICAL DIFFERENTIAL PROFILE MEASUREMENT APPARATUS AND PROCESS

[75] Inventors: Huizong Lu, Coconut Creek; Ali Reza Taheri, Boca Raton, both of Fla.

[73] Assignee: International Business Machines Corporation, Armonk, N.Y.

[*] Notice: The term of this patent shall not extend beyond the expiration date of Pat. No. 5,699,160.

[21] Appl. No.: 710,807

[22] Filed: Sep. 23, 1996

[51] Int. Cl.$^6$ .................................................. G01B 9/02
[52] U.S. Cl. ................................................ 356/351; 356/360
[58] Field of Search ................................. 356/345, 351, 356/359, 353, 360

[56] References Cited

U.S. PATENT DOCUMENTS

| | | | |
|---|---|---|---|
| 4,298,283 | 11/1981 | Makosch et al. | 356/351 |
| 4,320,973 | 3/1982 | Fortunato et al. | 356/346 |
| 4,534,649 | 8/1985 | Downs | 356/351 |
| 4,770,532 | 9/1988 | Ito . | |
| 4,844,616 | 7/1989 | Kulkarne et al. | 356/351 |
| 5,122,648 | 6/1992 | Cohen et al. | 250/201.3 |
| 5,469,259 | 11/1995 | Golby et al. | 356/351 |
| 5,557,399 | 9/1996 | de Groot | 356/351 |

FOREIGN PATENT DOCUMENTS 1392395  4/1975  United Kingdom .

OTHER PUBLICATIONS

T. Bayer and G. Makosch, Photolithgraphic Process Control by Optical Phase Monitoring of Latent Images in Photoresist, *IBM Tech. Disclosure Bulletin*, vol.34, No. 10A, Mar., 1992, pp. 140–143.

U. Frank–Schmidt and G. Makosch, Interferometric Method of Checking the Overlay Accuracy in Photolithographic Exposure Processes, *IBM Tech. Disclosure Bulletin*, vol. 32, No. 10B, Mar. 1990, pp. 214–217.

G. Makosch, System for Stepless Beam Splitting, *IBM Tech. Disclosure Bulletin*, vol. 30, No.11, Apr. 1988, pp. 249–250.

H. Korth and F. Schedwie, Analyzing Optical Phase Structures, *IBM Tech. Disclosure Bulletin*, vol. 24, No. 6, Nov., 1981, pp. 3094–3095.

*Primary Examiner*—Robert Kim
*Attorney, Agent, or Firm*—Richard Tomlin; Ronald V. Davidge

[57] ABSTRACT

An interferometer forms a pair of projected sub-beams by decomposing a single coherent, linearly-polarized beam. These sub-beams are focussed by an objective lens onto a pair of test spots on a test surface. The reflections of these sub-beams are recombined to form an elliptically polarized return beam, which is broken into return sub-beams of opposing polarities in a polarizing beam splitter. The intensities of these return sub-beams are used to calculate a difference in height between the two test spots. When these test spots are aligned along a path of relative motion with the test surface, the resulting differences in height are added to form an accumulative profile of the test surface.

13 Claims, 1 Drawing Sheet

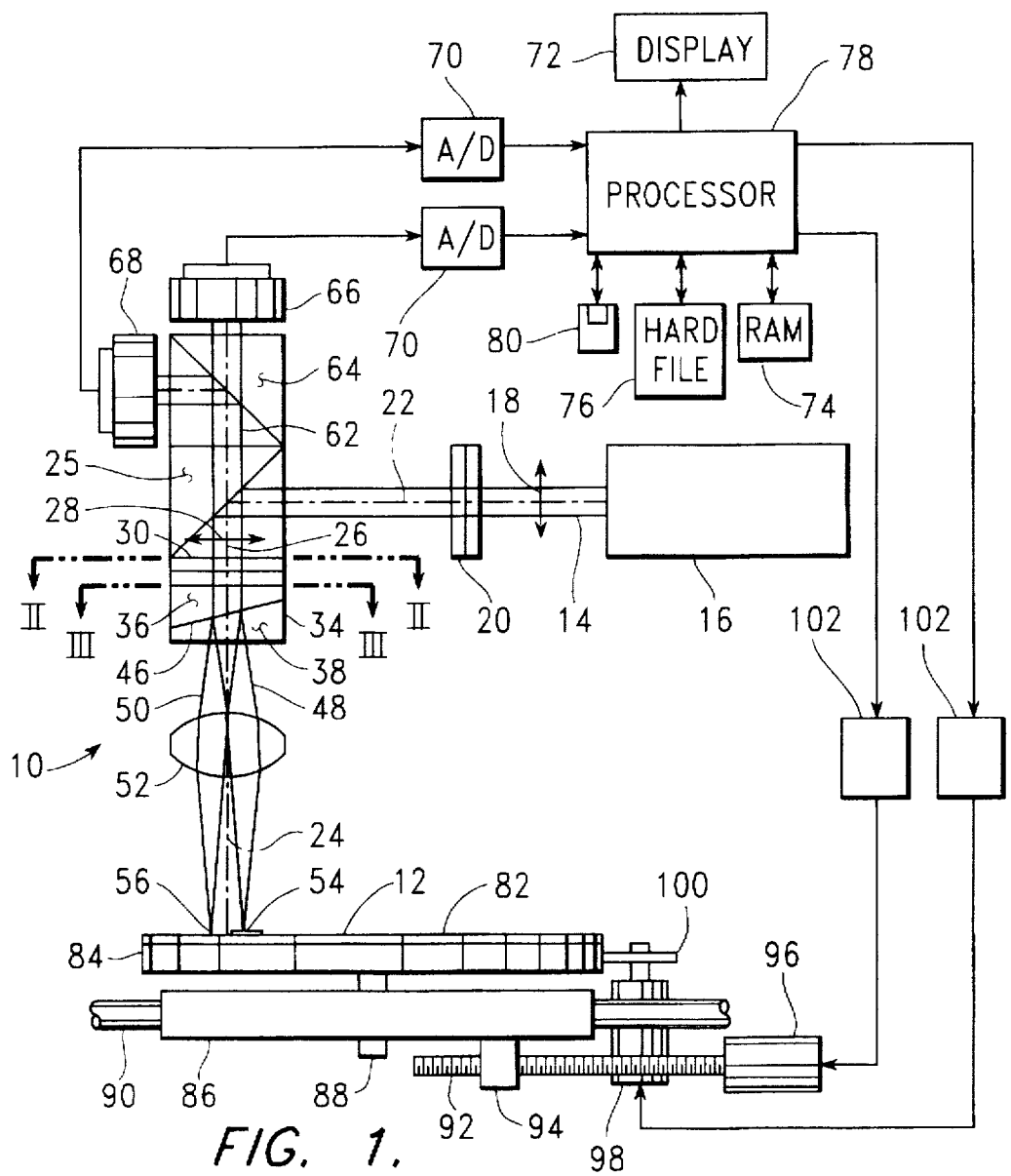
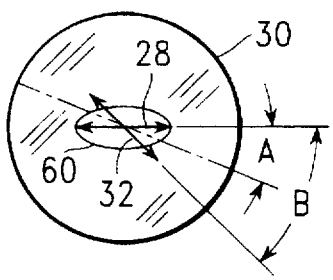
FIG. 2.
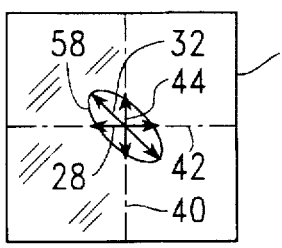
FIG. 3.
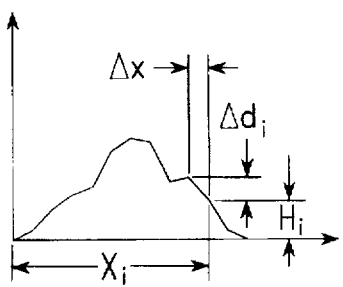
FIG. 4.

OPTICAL DIFFERENTIAL PROFILE MEASUREMENT APPARATUS AND PROCESS

CROSS REFERENCE TO A RELATED APPLICATION

A co-pending U.S. application Ser. No. 08/710,818, entitled "Apparatus for Optical Differential Measurement of Glide Height Above a Magnetic Disk," filed on the same day as the present application, and having a common assignee therewith, describes the use of an interferometer to measure changes in the glide height of a simulated magnetic head above a magnetic disk surface under test.

A co-pending U.S. application Ser. No. 08/710,806, entitled "Optical Apparatus for Inspecting Laser Texture," filed on the same day as the present application, and having a common assignee therewith, describes the use of an interferometer configured to measure the profile of textured spots on a disk in comparison to an adjacent flat surface.

A co-pending U.S. application Ser. No. 08/710,805, entitled "Optical Apparatus for Rapid Defect Analysis," filed on the same day as the present application, and having a common assignee therewith, describes apparatus including a first type of interferometer rapidly scanning a surface for defects and a second type of interferometer providing surface profiles of the defects.

BACKGROUND OF THE INVENTION

1. Field of the Invention

This invention relates to an apparatus and method for acquiring and analyzing data from an interferometer, and, more particularly, to a method for analyzing the relative height of adjacent points on a surface imaged by an interferometer as the surface is moved in a scanning motion.

2. Background Information

Semiconductor wafers and magnetic disks, such as those used to store data in computer systems, have become very sensitive to surface flatness and other parameters determining surface quality. The surfaces of such devices need to be inspected with a high degree of accuracy for anomalies at a very high throughput rate to match the capabilities of the equipment used to manufacture such devices.

Thus, surface profilers have become key instruments used in the manufacture of such devices, being widely used to study surface topography, structure, roughness, and other characteristics. Surface profilers are categorized into a first class of instruments, providing contact measurements with a probe that physically contacts the surface being measured, and a second class of instruments, providing non-contact measurements without physically contacting the surface being measured. In many applications, non-contact measurements are strongly preferred to avoid contamination and mechanical damage to the surface being measured, and to allow inspection at a high surface speed.

An example of an instrument providing non-contact surface measurements is a surface profile interferometer, which is particularly used for determining the roughness of a surface or the height of a step change in the thickness of a part being measured. Such a step change may be caused, for example, by the application of a metal film to a substrate in the manufacture of a printed circuit board or an integrated microcircuit. In general terms, an interferometer is an optical instrument in which two beams of light derived from the same monochromatic source are directed along optical paths of different length, in which the difference in length determines the nature of an interference pattern produced when the light beams are allowed to interfere. Since the beams of light are derived from the same monochromatic source, they are identical in wavelength. At equal path distances from the source, they are also in phase with one another. Phase differences between the beams therefore result only from differences in path length.

The phenomenon of light wave interference results from the mutual effect of two or more waves passing through the same region at the same time, producing reinforcement at some points and neutralization at other points, according to the principle of superposition.

With a photoelectric shearing interferometer, the height of a step change in a test surface may be measured using polarized light passed through a slit, through a Wollaston prism, and through a microscope objective lens, to form two images of the slit, with one image on each side of the step change. The beams reflected by the test surface pass through the lens and the prism, with an image being formed by two orthoganally polarized beams. The phase difference between these beams, which is determined by the height of the step, may be measured by the linear movement of a weak lens in a lateral direction (transverse to the beam) until the phase difference is exactly cancelled, as determined by the use of an electro-optic modulator, an analyzer, a photomultiplier, and a phase-sensitive detector, which are used together to detect the phase equality of the two interfering beams. The accuracy of the system depends on the precision to which the linear movement of the weak lens can be measured. Thus, a difference in phase between two orthogonal polarizations is measured, with the beams laterally displaced by the Wollaston prism, so that the system is not a common-path interferometer.

The Wollaston prism makes use of the phenomenon of double refraction or birefringence, through which a crystal of a transparent anisotropic material refracts orthogonally polarized light beams at different angles. Crystals such as calcite, quartz, and mica exhibit this property. A Wollaston prism includes two wedge-shaped segments held together with adjacent polished surfaces extending along a plane at an oblique angle to the optical axis of the device. The outer surfaces of the Wollaston prism lie along planes perpendicular to the optical axis of the device. The two segments of the Wollaston prism are composed of a birefringent material, with the crystal axes of the material lying perpendicular to each other and to the optical axis of the device.

For example, if a beam of light consisting of two sub-beams polarized orthogonally to each other is directed along the optical axis of the device to a Wollaston prism, the two beams will not be refracted at the initial surface of the prism, since it lies perpendicular to the direction of both beams. However, when the two beams reach the oblique surfaces inner surfaces of the two segments of the prism, refraction will occur, with the two beams being refracted at different angles because of the birefringence of the material of which the prism segments are composed. When the two beams reach the opposite external side of the prism, they are again refracted.

While the above discussion describes a Wollaston prism comprising two wedges of birefringent material, it is possible and often advantageous to form a prism of this kind using three or more such wedges, joined at two or more oblique planes. When this is done, the outer surfaces of the prism remain perpendicular to the optical center of the device.

Thus, a number of methods have been developed for using interferometers to provide accurate measurements of very small surface features. However, since these methods are based on rather elaborate and painstaking processes in which a very small surface area is held in place to be viewed through an interferometer, they are difficult to apply to the materials of a mass production process making, in large volumes, parts which would benefit from inspection by means of interferometry.

What is needed is a way to apply a scanning process allowing a relatively large test surface to be examined without stopping for the measurement of individual areas, while providing quantitative data on step changes and on the slope of defect walls in real time during the scanning process.

DESCRIPTION OF THE PRIOR ART

U.S. Pat. No. 5,469,259 describes an interferometer of a common mode shearing type, which produces a pair of sheared optical beams both incident on a surface being inspected. These shared beams are produced by a compound Wollaston prism, which projects a real splitting point in the rear focal plane of a microscopic objective. The objective lens forms interferograms of portions of the surface being inspected on both an area array CCD sensor, used for static surface acquisition, and a line scan CCD sensor, used for moving surface acquisition as the test surface is moved, or scanned, past the objective lens. A dual-purpose illumination arm provides different forms of illumination required for the static (area) and moving (scanning) processes.

When the scanning process is to be performed, the interferometer is adjusted to produce a dark field interferogram on the line scan CCD sensor, with flat areas of the surface being scanned remaining dark, while anomalies, whether raised or depressed, appear as bright areas. Thus, while the scanning process is useful for determining the locations of anomalies, to a degree, their areas, many important features of an individual anomaly, such as whether it is raised or depressed and its height or depth cannot be determined.

On the other hand, when the interferometer of U.S. Pat. No. 5,469,259 is used in the static mode, analyzing a stationary interferometric image projected on the area array CCD sensor, the height or depth of the anomaly and various details of its shape can be readily determined. The disadvantage of this mode is that the surface under test must be held stationary as each anomaly is checked. Thus, a time to move between anomalies must be added to the time required for measurements and calculations, making the measurement of an individual anomaly take as long as 0.8 sec.

What is needed is an non-contact, optical method for making height and depth measurements of anomalies while scanning, without requiring that the motion of the test sample be stopped.

SUMMARY OF THE INVENTION

In accordance with one aspect of the invention, there is provided surface inspection apparatus for determining a profile of a surface under test. The surface inspection apparatus includes a laser, optical apparatus, a polarizing beam-splitter, and first and second photodetectors. The laser produces a coherent, linearly-polarized beam, which is decomposed within the optical apparatus to form first and second projected sub-beams. The first projected sub-beam is linearly polarized in a first direction, while the second projected sub-beam is linearly polarized in a second direction, opposite the first direction. The first and second projected sub-beams are projected to first and second test spots on the surface under test, which extend along the surface under test in a spaced-apart relationship. The first and second projected sub-beams, after reflection from the first and second test spots, are recombined into a single, elliptically polarized return beam, which is split within the beam splitter into a first return sub-beam, polarized in a third direction, and a second return sub-beam, polarized in a fourth direction, perpendicular to the third direction. The first and second photodetectors measure intensity of the first and second return sub-beams, respectively.

BRIEF DESCRIPTION OF THE DRAWINGS

FIG. 1 is a schematic elevation of an interferometer built in accordance with the present invention;

FIG. 2 is a schematic plan view of a half-wave plate in the interferometer of FIG. 1, taken as indicated by section lines II—II in FIG. 1 to show the polarization orientations of coherent beams travelling therethrough;

FIG. 3 is a schematic plan view of a Wollaston prism in the interferometer of FIG. 1, taken as indicated by section lines III—III in FIG. 1 to show the polarization orientations of laser beams travelling therethrough; and FIG. 4 is a graphical representation of a process for determining the profile of a relatively large anomaly in a test surface by combining the results of a number of measurements.

DETAILED DESCRIPTION

FIG. 1 is a schematic elevation of an interferometer 10 built in accordance with the present invention. Within this apparatus, a test surface 12 is illuminated from a beam 14 projected from a laser unit 16. A laser unit having an output beam with a wavelength of 532 nanometers has proven to be satisfactory in this application. This beam leaves the laser unit vertically polarized, as indicated by arrow 18. A half-wave plate 20 is rotated about the axis 22 of the laser beam 14 to provide a fine adjustment of the vertical polarization of the laser beam 14 projected therethrough. After passing through half-wave plate 20, a portion of the laser beam 22 is deflected downward, along an optical axis 24 of the interferometer 10, within a non-polarizing beamsplitter 25. A portion of the laser beam 14 is wasted, being transmitted through the beamsplitter 25 instead of reflected therein. The downward-directed reflected laser beam 26, which is horizontally polarized as indicated by arrow 28, is projected through a second half-wave plate 30.

FIG. 2 is a schematic plan view of the second half-wave plate 30, taken as indicated by section lines II—II in FIG. 1, to show the polarization orientations of laser beams projected therethrough. The transmission of linearly polarized light through a half-wave plate results in the rotation of the angle of polarization through an angle which is twice the angle between the direction of polarization and the crystal axis of the material composing the half-wave plate. In the example of half-wave plate 30, the crystal axis is at a 22.5 degree angle, indicated as angle A, from the polarization direction, indicated by arrow 28, of the downward-reflected beam 26 (shown in FIG. 1). Therefore, in passing through half-wave plate 30, the direction of polarization of this laser beam is rotated through a 45-degree angle, indicated as angle B, to have the orientation indicate by arrow 32.

FIG. 3 is a schematic plan view of a Wollaston prism 34, directly below the second half-wave plate 30, taken as indicated by section lines III—III in FIG. 1, to show the polarization of laser beams traveling through the upper portion of the prism 34.

Referring to FIGS. 1 and 3, the Wollaston prism 34 is composed of a pair of wedge-shaped segments 36, 38 of crystalline material having crystal axes 40, 42 which are perpendicular to one another and to the optical axis 24 of the interferometer 10. Thus, the downward deflected laser beam 26 enters the Wollaston prism 34 being polarized in a direction at a 45-degree angle from the optical axis of the upper wedge-shaped segments 36, and is therefore decomposed into a pair of sub-beams of equal intensity, polarized in the mutually-perpendicular directions indicated by arrows 28, 44. Since the crystalline material forming each segment 36, 38 of the Wollaston prism 34 is birefringent, refracting beams polarized at different angles in different directions, the two sub-beams travelling downward therethrough, being polarized perpendicularly to one another, as indicated by arrows 28, 44, are refracted differently at the interface 46 between the segments 36, 38. In general, the Wollaston prism separates the two sub-beams exiting its lower surface by a deviation angle, which is a function of the wavelength of the laser beam, the indices of refraction of the materials of which the wedge-shaped portions 36, 38, and the angle at which the interface surface 46 is sloped.

In general, a Wollaston prism may be composed of a number of wedge-shaped segments, from a single segment up to three or more segments. In a Wollaston prism having one or two segments, the sub-beams diverge from a surface, such as interface surface 46, which is called a split point. In a Wollaston prism having three or more segments, the sub-beams are typically brought back together, to cross one another at a cross-over point between the Wollastom prism and the objective lens. If there is no cross-over point, the split point is in the back focal plane of the objective lens. If there is a cross-over point, the final cross-over point is in the back focal plane of the objective lens.

In this way, a right sub-beam 48 having a first direction of polarization and a left sub-beam 50, having a direction of polarization perpendicular to that of right sub-beam 48 are formed. Both of these sub-beams 48, 50 pass through an objective lens 52, being focussed on test surface spots 54, 56, respectively. After reflecting off the test surface spots 54, 56 the sub-beams 48, 50 return upward through objective lens 52 and Wollaston prism 34, being recombined at the upper wedged-shaped segment 36 of the prism 34. During the process of reflection off the spots 54, 56, the directions of polarization remain as indicated by arrows 28, 44.

In the example of FIG. 1, test surface spot 54 is raised above the level of test surface spot 56. Since the distances travelled by the sub-beams 48, 50 are different, the times required for projection and reflection from the test spots 54, 56, respectively, are different, producing a phase-shift between the two sub-beams 48, 50 as they are reflected back to the Wollaston prism 34. When these reflected sub-beams are recomposed within the Wollaston prism 34, due to this phase shift, they form an elliptically polarized beam, having major and minor axes extending at 45-degree angles to the crystal axes 40, 42 of the materials making up the Wollaston prism 34. In FIG. 3, the polarization of this recomposed beam is indicated by an ellipse 58.

Referring to FIGS. 2 and 3, as the recomposed beam is transmitted upward through half-wave plate 30, its elliptical polarization is rotated to have major and minor axes extending in the direction of arrow 28 and in the direction perpendicular thereto, as indicated by an ellipse 60. The relative intensities along the major and minor axes of ellipse 60 are determined by the phase-shift between the sub-beams 48, 50 returning after reflection from the test spots 54, 56.

Referring again to FIG. 1, the recomposed beam is transmitted upward from half-wave plate 30 into the non-polarizing beamsplitter 25, with the transmitted portion 62 of this recombined beam being used for subsequent measurements, as the portion of this beam reflected within the beamsplitter 25 is discarded. The elliptical polarization indicated by ellipse 60 in FIG. 2 is retained. The transmitted portion 62 of this beam is next split within a polarizing beamsplitter 64, with a portion of the beam 62 polarized in the direction indicated by arrow 28 being transmitted into a first photodetector 66, while a portion of the beam 62 polarized in the direction of arrow 44 (shown in FIG. 3) is reflected into a second photodetector 68.

The output of each photodetector 66, 68 is provided as an input to a corresponding analog to digital convertor 70, which in turn provides an input to a computer processor 72. This processor 72 is a conventional device connected to conventional devices, such as a system memory 74, a hardfile 76, and a display unit 78. Programs for execution within the processor 72 are loaded into memory 74 from a diskette 80.

Referring to FIGS. 1–3, the relative illumination intensities measured at photodetectors 66, 68 provide an indication of relative intensities of the polarization along the major and minor axes of the elliptical polarization indicated by ellipse 60, and hence of the phase shift between the returning sub-beams 48, 50. This phase shift is a function of the relative heights of test spots 54, 56 and of parameters within the interferometer 10. The elliptically polarized return beam exiting half-wave plate 30 may be mathematically broken into an X-vector, $V_x$, describing light polarized in the direction indicated by arrow 28, and a Y-vector, $V_y$, describing light polarized in the direction indicated by arrow 44. The values of these vectors are given as a function of the time variable, t, by:

$$V_x = A_0 \sin(\omega t + kL + 2kd + \phi_0) \quad (1)$$

$$V_y = A_0 \sin(\omega t + kL) \quad (2)$$

Thus, the X- and Y-vectors have the same amplitude, $A_0$, differing only in phase angle. In these equations, $\omega$ is the angular frequency of the laser beam, in radians per second, L is the original length of the light path, which does not matter because it has the same effect on both equations (1) and (2), d is the height difference which is being measured by this process, $\phi_0$ is an original phase angle, which is the phase angle provided by the apparatus when the test spots 54, 56 are at the same height, and k is a wave number, which is defined as follows:

$$k = \frac{2\pi}{\lambda} \quad (3)$$

In this expression, $\lambda$ is the wavelength of the laser beam. To simplify the following mathematical derivation, these equations are rewritten using complex notation as:

$$V_x = A_0 e^{i(\omega t + kL + 2kd + \phi_0)} \quad (4)$$

$$V_y = A_0 e^{i(\omega t + kL)} \quad (5)$$

After passing through the beamsplitter 25, the elliptically polarized return beam 62 is broken into sub-beams within polarizing beamsplitter 64. Since the beamsplitter 25, being a non-polarizing type, handles differing polarities in the same way, losses in the transmission through this beamsplitter 25 are not considered, as it is determined that the light level at photodetector 68 is given by:

$$V_s = V_x \cos 45° + V_y \cos 45° \qquad (6)$$

$$V_s = \frac{\sqrt{2}}{2} A_0 [e^{i(\omega t + kL + 2kd + \phi_0)} + e^{i(\omega t + kL)}] \qquad (7)$$

Similarly, the light level at photodetector 66 is given by:

$$V_p = \frac{\sqrt{2}}{2} A_0 [e^{i(\omega t + kL + 2kd + \phi_0)} - e^{i(\omega t + kL)}] \qquad (8)$$

The light intensity measured at photodetector 68 is obtained by multiplying $V_s$ times its conjugate, resulting in the following equation:

$$I_1 = \frac{A_0^2}{2} [e^{i(\omega t + kL + 2kd + \phi_0)} + e^{i(\omega t + kL)}][e^{-i(\omega t + kL + 2kd + \phi_0)} + e^{-i(\omega t + kL)}] \qquad (9)$$

Next, $I_0$ is defined as equal to the square of $A_0$, the imaginary portion of the above equation is eliminated, and the real portion of the equation is rewritten as:

$$I_1 = \frac{I_0}{2}[2 + \cos(2kd + \phi_0)] \qquad (10)$$

$$I_1 = I_0 \cos^2\left(kd + \frac{\phi_0}{2}\right) \qquad (11)$$

Similarly the beam intensity at sensor 66 is given by:

$$I_2 = I_0 \sin^2\left(kd + \frac{\phi_0}{2}\right) \qquad (12)$$

The preceding discussion assumes that the incoming laser beam 14, which is directed downward at the half-wave plate 30, is perfectly polarized in the direction of arrow 28 when it enters the half-wave plate 30. In other words, the preceding discussion assumes the following equations to be true:

$$I_x = I_0 \qquad (13);$$

$$I_y = 0 \qquad (14)$$

A more realistic mathematical model is given by the following equations, in which τ has a value, depending on various aspects of the apparatus, between 0 and 1. If the input beam from the laser entering half-wave plate 30 is entirely polarized in the x-direction indicated by arrow 28, τ is equal to one. If this beam is entirely polarized in the y-direction indicated by arrow 44 (shown in FIG. 3), τ is equal to zero.

$$I_x = \tau I_0 \qquad (15)$$

$$I_y = (1-\tau)I_0 \qquad (16)$$

Under these conditions, the illumination intensity, $I_1$, of the beam impinging on photodetector 68, and the illumination intensity, $I_2$, of the beam impinging on photodetector 66, are given by the following equations:

$$I_1 = \Gamma I_0 \cos^2\left(kd + \frac{\phi_0}{2}\right) + (1 - \Gamma)I_0 \sin^2\left(kd + \frac{\phi_0}{2}\right) \qquad (17)$$

$$I_2 = \Gamma I_0 \sin^2\left(kd + \frac{\phi_0}{2}\right) + (1 - \Gamma)I_0 \cos^2\left(kd + \frac{\phi_0}{2}\right) \qquad (18)$$

The mathematics associated with these intensities is simplified by considering the sum and differences of Equations (17) and (18), yielding the following results:

$$I_1 - I_2 = (2\tau - 1)I_0 \cos(2kd + \phi_0) \qquad (19)$$

$$I_1 + I_2 = I_0 \qquad (20)$$

A differential intensity parameter is formed by dividing the difference between the illumination intensity signals by their sum. Thus, this differential intensity parameter S is given by the following equation:

$$S = \frac{I_1 - I_2}{I_1 + I_2} = (2\Gamma - 1)\cos(2kd + \phi_0) \qquad (21)$$

The interferometer 10 can be adjusted, particularly by moving the Wollaston prism 34 in the directions indicated by arrow 28, so that $\phi_0$ is equal to 0, π/2, or another convenient value. Such an adjustment may, for example, be made so that, when a flat test surface 12 is imaged, the output values of the two photodetectors 66, 68 are equal.

Next $\phi_0$ is set to −π/2, so that S is expressed as:

$$S = (2\Gamma - 1)\sin 2kd = (2\Gamma - 1)\sin\left(\frac{4\pi d}{\lambda}\right) \qquad (22)$$

With this substitution, S has the same sign as d. Equation (22) is in a form which can be solved for the distance d, yielding:

$$d = \left(\frac{\lambda}{4\pi}\right) \arcsin\left(\frac{S}{2\Gamma - 1}\right) \qquad (23)$$

This equation holds true as long as the following relationships are met:

$$0 \leq \tau \leq 1 \qquad (24);$$

$$\tau \neq \tfrac{1}{2} \qquad (25)$$

Thus, during measurement processes, a program is executed in processor 72 to determine the distance in height between the two test spots 54, 56, indicated as d in the equations, by substituting the illumination intensity values, indicated in the equations as $I_1$ and $I_2$ in the equations, measured by photodetectors 66, 68, into the equations (22) and (23).

These measurements and calculations are preferably made as the test surface 12 is driven in a scanning direction parallel to its flat portions. In the example of FIG. 1, the test surface 12 is an upper surface of a disk 82 being examined. The disk 82 is mounted atop a turntable 84, which is mounted to rotate on a carriage 86 about a shaft 88. The carriage 86 is in turn mounted to slide on a pair of parallel guide shafts 90, being driven by a leadscrew 92, engaging an internally threaded block portion 94 of the carriage 86. The leadscrew 92 is driven by a motor 96. Rotary motion of the turntable 84 is achieved using a second motor 98 driving a wheel 100 engaging an outer surface of the turntable 84. The motors 96, 98 are driven to scan the surface 82 past the projected sub-beams according to a pre-determined path by means of driver circuits 102 in response to a program routine executing in processor 72. Since, during scanning, the output levels of photodetectors 66, 68 may continuously change, these outputs are preferably examined by sampling on a periodic basis. This sampling process may obtain an instant level of intensity measurement or an average intensity level occurring over a short time, such as the time between samples.

In a preferred mode of operation, relative motion is established between the test surface 12 and the test points 54, 56 in the direction aligned with these test points 54, 56. When the apparatus is operating in this mode, the height calculations for individual segments of an anomaly are summed to obtain overall profile data for the anomaly. Relative motion may be established by holding the interferometer 10 stationary while the test surface 12 is moved, as in the example of FIG. 1, by moving the interferometer as the test surface remains stationary, or by moving the interferometer and test surface in different directions, which may, for example, be perpendicular to one another.

In an alternative mode of operation, relative motion is established between the test surface 12 and the test points 54, 56 in a direction perpendicular to a line between these test points 54, 56. When the apparatus is operating in this mode, the slopes of sides of individual anomalies may be examined.

FIG. 4 is a graphical representation of the process of determining the profile of a relatively large anomaly in a test surface with operation of the apparatus in the preferred mode defined above. Each measurement made yields a calculated change in height, indicated as $\Delta d_j$, occurring across an incremental distance, indicated as $\Delta x$, which is equal to the distance between test spots 54, 56. For example, the scanning motion occurs at a constant speed, with the outputs of photodetectors 66, 68 being sampled periodically at times corresponding to scanning through the distance $\Delta x$. This distance may be, for example, 2 microns. The horizontal and vertical coordinates to a measured point i on the surface of the anomaly, indicated as $X_i$ and $H_j$, respectively, are calculated using the following equations:

$$X_i = i\Delta x \quad (26)$$

$$H_i = \sum_{j=0}^{i} \Delta d_j \quad (27)$$

Thus, the program executing in processor 72 also performs a profile development function by calculating horizontal distance and height information using the equations (26) and (27). While the term "height" is used to indicate a vertical distance above the nominally flat surface of the surface 12 under test, or an upward sloping portion of an anomaly, it is understood that negative values for "height" indicate a vertical distance below the nominally flat surface of the surface 12 under test or a downward sloping portion of an anomaly. The lateral resolution depends on the sub-beam spot sizes and on the separation distance between the two beams. The vertical resolution depends on the signal-to-noise ratio implicit in the calculation of the differential intensity parameter, S. This signal-to-noise ratio in turn depends on the stability of the system, on the laser intensity and level of fluctuation, on the contrast ration, and on the dark current, noise levels, and sensitivity of the photodetectors 66, 68. Using apparatus of this sort, a vertical resolution of 1 nanometer can be achieved.

While the invention has been described in its preferred form or embodiment with some degree of particularity, it is understood that this description has been given only by way of example and that numerous changes in the details of construction, fabrication and use, including the combination and arrangement of parts, may be made without departing from the spirit and scope of the invention.

What is claimed is:

1. Surface inspection apparatus for determining a profile of a surface under test, wherein said surface inspection apparatus comprises:

a laser producing a coherent, linearly polarized beam;

optical apparatus, wherein said coherent, linearly polarized beam is decomposed into first and second projected subbeams, with said first projected sub-beam being linearly polarized in a first direction, with said second projected sub-beam being linearly polarized in a second direction, perpendicular to said first direction, wherein said first projected sub-beam is projected to a first test spot on said surface under test, wherein said second projected sub-beam is projected to a second test spot on said surface under test, with said first and second test spots extending along said surface under test in a spaced-apart relationship, wherein said first and second projected sub-beams, after reflection from said first and second test spots, are recombined into a single, elliptically polarized return beam having a first principle axis at a direction midway between said first and second directions and a second principle axis perpendicular to said first principle axis;

a polarizing beamsplitter in which said elliptically polarized return beam is split, with a portion of said return beam polarized along said first principle axis forming a first return sub-beam and with a portion of said return beam polarized along said second principle axis forming a second return sub-beam;

a first photodetector measuring intensity of said first return sub-beam; and a second photodetector measuring intensity of said second return sub-beam, a computer processor in which a first routine is running, wherein said computer processor operates in response to a first intensity input from said first photodetector and a second intensity input from said second photodetector, and wherein said first routine calculates an output value representing a difference in height between first and second test spots solely as a function of said first and second intensity inputs and of a wavelength and polarization angle of said coherent, linearly polarized beam.

2. The surface inspection apparatus of claim 1, comprising in addition surface drive means for establishing relative movement, along a pre-determined path, between said surface under test and said test spots.

3. The surface inspection apparatus of claim 2 wherein said first and second test spots lie on said surface under test in said spaced-apart relationship, extending in a direction perpendicular to said pre-determined path.

4. The surface inspection apparatus of claim 2, wherein said first and second test spots lie on said surface under test in said spaced-apart relationship, extending along said pre-determined path.

5. The surface inspection apparatus of claim 4, wherein said first routine performs a profile development function adding subsequently-determined differences in height to obtain a cumulated height.

6. The surface inspection apparatus of claim 1, wherein said optical apparatus includes:

a Wollaston prism, wherein said coherent, linearly polarized beam is decomposed into said first and second projected sub-beams, and wherein said first and second projected sub-beams, after reflection from said first and second test spots, are recombined into said single, elliptically polarized return beam; and an objective lens, disposed between said Wollaston prism and said test surface, wherein said objective lens focusses said first projected sub-beam on said first test spot and said second projected sub-beam on said second test spot.

7. The surface inspection apparatus of claim 6:

wherein said Wollaston prism includes a first segment having a crystal axis extending in said first direction and a second segment having a crystal axis extending in said second direction;

wherein said coherent, linearly polarized beam is directed into said optical apparatus being polarized in said first direction; and wherein said optical apparatus additionally includes a half-wave plate through which said coherent, linearly polarized beam is directed into said Wollaston prism, with said half-wave plate rotating polarization of said coherent, linearly polarized beam into a direction midway between said first and second directions.

8. The surface inspection apparatus of claim 1, comprising in addition surface drive means for establishing relative movement, along a pre-determined path, between said surface under test and said test spots, wherein said first and second test spots lie on said surface under test in said spaced-apart relationship, extending along said pre-determined path, and wherein said first routine performs a profile development function adding subsequently-determined differences in height to obtain a cumulated height.

9. The surface inspection apparatus of claim 1, wherein said first routine calculates said difference in height as a function of an intensity parameter, with said intensity parameter being a difference between said first and second intensity inputs divided by a sum of said first and second intensity inputs.

10. The surface inspection apparatus of claim 1, wherein said function is a product of a wavelength of light from said laser, divided by a constant, times an arcsine of said intensity parameter divided by an input polarization parameter reflecting polarization conditions of light from said laser.

11. A process for determining a profile of a surface under test, wherein said process comprises the steps of:

(a) exposing a first test spot on said surface under test to a first projected sub-beam, linearly polarized in a first direction, while a second test spot on said surface under test is exposed to a second projected sub-beam, linearly polarized in a second direction, perpendicular to said first direction, wherein said first and second test spots extend along said surface under test in a spaced-apart relationship, wherein said first and second projected sub-beams are formed by decomposing a single coherent, linearly-polarized beam, wherein after reflection from said surface under test, said first and second projected sub-beams are recombined into an elliptically polarized return beam having a first principle axis midway between said first and second directions and a second principle axis perpendicular to said first principle axis, wherein said elliptically polarized return beam is split into a first return sub-beam and a second return sub-beam, wherein a portion of said return beam polarized along said first principle axis forms said first return sub-beam, wherein a portion of said return beam polarized along said second principle axis forms said second return sub-beam, wherein intensity of said first return sub-beam is measured within a first photodetector, and wherein intensity of said second sub-beam is measured within a second photodetector; and (b) calculating, within computing equipment, a difference in heights of said first and second test spots, in response to a first intensity measured by said first photodetector and a second intensity measured by said second photodetector, solely as a function of said first and second intensities and of a wavelength and polarization angle of said coherent, linearly polarized beam.

12. The process of claim 11:

wherein said step (a) occurs with relative motion between said surface under test and said test spots, with outputs of said first and second photodetectors being periodically sampled; and wherein said step (b) occurs following each sample of outputs of said first and second photodetectors.

13. The process of claim 12:

wherein said first and second test spots are aligned along a path of said relative motion; and wherein said process additionally comprises a step of adding, within said computing equipment, a result of a calculation of said difference in height between said first and second test spots to an accumulative total thereof.

* * * * *